United States Patent [19]

Huang et al.

[11] Patent Number: 5,066,592
[45] Date of Patent: Nov. 19, 1991

[54] TRIGRAMIN - A PLATELET AGGREGATION INHIBITING POLYPEPTIDE

[75] Inventors: Tur-Fu Huang, Taipei, Taiwan; Stefan Niewiarowski, Narberth; John C. Holt, Philadelphia, both of Pa.; Hanna Lukasiewicz, Warsaw, Poland

[73] Assignee: Temple University of the Commonwealth System of Higher Education, Philadelphia, Pa.

[21] Appl. No.: 584,820

[22] Filed: Sep. 19, 1990

Related U.S. Application Data

[63] Continuation of Ser. No. 165,661, Mar. 8, 1988, abandoned, which is a continuation-in-part of Ser. No. 121,972, Nov. 18, 1987, abandoned.

[51] Int. Cl.$^5$ .................. C12N 5/08; A61K 37/02; C07K 7/10; C07K 15/08
[52] U.S. Cl. .................. 435/240.2; 435/240.1; 514/12; 514/21; 514/822; 530/324; 530/856
[58] Field of Search ............... 530/324, 856; 514/12, 514/822, 21; 435/240.2, 240.2

[56] References Cited

U.S. PATENT DOCUMENTS 4,683,291  7/1987  Zimmerman et al. ............ 530/326

OTHER PUBLICATIONS

Ouyang et al., "Potent Platelet Aggregation Inhibitor from Trimeresurus gramineus Snake Venom", Biochim. Biophys. Acta., 757:332-341 (1983).
Huang et al., "Action Mechanism of the Potent Platelet Aggregation Inhibitor from Trimeresurus gramineus Snake Venom", Thrombos. Res. 33:125-138 (1984).
Huang et al., "Isolation and Characterization of Trigramin, A Highly Specific Inhibitor of Fibrinogen Binding to Glycoprotein IIb/IIIa Complex on the Platelet Surface", Blood:68 (5), Suppl. 1, p. 318, Abs. #1149 (Nov. 1986).
Huang et al., "Characterization of Fibrinogen Receptors Associated with Glycoprotein IIb/II (GP IIb/G-PIII) Complex by Trigramin . . . ", Federation Proceedings 46 (4), Abstract #5819 (Mar. 5, 1987).
Huang et al., "Characterization of Fibrogen Receptors Associated with Glycoprotein IIb/III (GP IIb/GP III) Complex by Trigramin . . . ", Thromb. Haemostas. 58 (1), 196, Abstract #724 (Jul. 6, 1987).
C. Ouyang et al., "Inhibition of Platelet Aggregation by 5-Nucleotidase Purified from *Trimeresurus–Gramineus* Snake Venom", Toxicon, vol. 21, No. 4, pp. 491-501 (1983).
C. Ouyang et al., "A Potent Platelet Aggregation Inhibitor Purified from *Akistrodon–Halys* (Mamushi) Snake Venom", Toxicon, vol. 21, No. 6, pp. 797-804 (1983).
C. Ouyang et al., "A Potent Platelet Aggregation Inducer from *Trimeresuru Gramineus* Snake Venom", Biochimica et Biophysica Acta, vol. 761, pp. 126-134 (1983).
T. Huang et al., "Mechanism of Action of the Platelet Aggregation Inhibito Purified from *Agkistrodon–Halys* (Mamushi) Snake Venom", Toxicon, vol. 22, No. 2, pp. 243-251 (1984).
C. Ouyang et al., "Effect of the Purified Phospholipases-$A_2$ from Snake and Bee Venoms on Rabbit Platelet Function", Toxicon, vol. 22, No. 5, pp. 705-718 (1984).

(List continued on next page.)

*Primary Examiner*—John Doll
*Assistant Examiner*—Christina Chan
*Attorney, Agent, or Firm*—Seidel, Gonda, Lavorgna & Monaco

[57] ABSTRACT

Trigramin, a 72-amino acid polypeptide, has the following amino acid sequence: EAGEDCDCGSPANPC-CDAATCKLIPGAQCGEGLCCDQCSFIEEGTV-CRIARGDDLDDYCNGRSAGCPRNPFH. The molecule is a potent inhibitor of fibrinogen binding to receptors expressed on the glycoprotein IIb/IIIa complex in the membrane of platelets. Trigramin is thus a potent inhibitor of fibrinogen-induced human platelet aggregation. It is useful in inhibiting the formation of hemostatic platelet plugs.

5 Claims, 5 Drawing Sheets

OTHER PUBLICATIONS

C. Ouyang et al., "Characterization of the Platelet Aggregation Inducer and Inhibitor from *Echis-Carinatus* Snake Venom", Biochima et Biophysica Acta, vol. 841, pp. 1-7 (1985).

C. Teng et al., "Action Mechanism of the Platelet Aggregation Inducer and Inhibitor from *Echis-Carinatus* Snake Venom", Biochimica et Biophysica Acta, vol. 841, pp. 8-14 (1985).

Y. Li et al., "A Platelet Function Inhibitor Purified from *Vipera Russell Siamensis* (Smith) Snake Venom", Toxicon, vol. 23, No. 6, pp. 895-903 (1985).

O. Ouyang et al., "Inhibition of Rabbit Platelet Aggregation by alpha-Fibrinogen Purified from *Calloselasma Rhodostoma* (Malayan Pit Viper) Venom", J. Formosan Med. Assoc. 84, pp. 1197-1206 (1985).

T. Kosugi et al., "Isolation of Platelet Aggregation Inhibitor from *Trimeresurus Flavoviridis* Snake Venom", The Snake, vol. 17, pp. 117-123 (1985).

Y. Li et al., "Mechanism of Action of the Platelet Function Inhibitor from *Vipera Russelli Siamensis* Snake Venom", Toxicon, vol. 24, No. 9, pp. 875-883 (1986).

C. Ouyang et al., "Platelet Aggregation Inhibitors from *Agkistrodon Acutus* Snake Venom", Toxicon, vol. 24, Nos. 11-12, pp. 1099-1106 (1986).

Huang et al., "Characterization of a Potent Platelet Aggregation Inhibitor from *Agkistrodon Rhodostoma* Snake Venom", Biochimica et Biophysica Acta, vol. 925, pp. 248-257 (1987).

Joubert et al., "Protein CM-2 from *Bitis arietans* (Puff Adder) Venom", Hoppe-Seyler's Z. Physiol. Chem., vol. 363, pp. 1087-1096 (1982).

TRIGRAMIN - A PLATELET AGGREGATION INHIBITING POLYPEPTIDE

Reference to Government Grant

The invention described herein was made, in part, in the course of work supported by National Institutes of Health grants HL 15226, HL 14217, and HL 36579, and by Fogarty Fellowship IF05 TW 03682-01.

REFERENCE TO RELATED APPLICATION

This is a continuation of co-pending application Ser. No. 165,661, filed Mar. 8, 1988, now abandoned, which is a continuation-in-part of application Ser. No. 121,972, filed Nov. 18, 1987, abandoned.

FIELD OF THE INVENTION

The invention relates to trigramin, a low molecular weight polypeptide which is a potent inhibitor of platelet aggregation.

BACKGROUND OF THE INVENTION

It is well established that interaction of fibrinogen with specific receptors associated with the glycoprotein IIb-IIIa (GPIIb-GPIIIa) complex is essential for platelet aggregation. Unstimulated platelets do not bind fibrinogen, and therefore do not aggregate in the circulation. When platelets are stimulated by agonists such as ADP, epinephrine, thrombin, or prostaglandin endoperoxides, fibrinogen receptors associated with the GPIIb-GPIIIa complex become exposed on the platelet surface, resulting in fibrinogen binding and subsequent platelet aggregation. The common interpretation is that ADP is an essential mediator of fibrinogen receptor exposure under physiological conditions. Evidence suggests that during tissue injury, ADP is formed in sufficient quantities to cause platelet aggregation.

Ouyang, C. and Huang, T., Biochim. Biophys. Acta 757:332-341 (1983) and Thrombos. Res. 33:125-138 (1984) report a crude preparation of a platelet aggregation inhibiting substance from *Trimeresurus gramineus* snake venom. The material was described as an acidic phospholipase A rich in aspartic acid, glutamic acid and cysteine, isolated by ion exchange chromatography and gel filtration. Ouyang et al. identified a single 12.4 kd band in the preparation by SDS-polyacrylamide gel electrophoresis and disc electrophoresis. They reported an estimated minimal molecular weight of 11,682 based upon 109 amino acid residues.

Despite the potency of the Ouyang et al. factor, the phospholipase A activity of the material renders it wholly unsuitable for clinical use owing to the hemolytic effect of phospholipase A on erythrocytes. Moreover, the impure material may contain one or more contaminating toxins from the raw snake venom. It is known that certain toxins found in snake venoms are toxic to humans in nanogram amounts.

SUMMARY OF THE INVENTION

We have found that the purported 109 amino acid protein of Ouyang et al. is but an impure mixture containing the actual platelet aggregation inhibiting factor.

We have obtained the platelet aggregation inhibiting factor from *T. gramineus* in substantially pure chemical form, free of phosphoilphase A contamination. The active platelet aggregation inhibiting factor, which we have named "trigramin", has been purified to chemical homogeneity.

Trigramin in substantially pure chemical form is a 72 amino acid polypeptide having the following amino acid sequence

EAGEDCDCGSPANPCCDAATCKLIPGAQC-
GEGLCCDQCSFIEEGTVCRIARGDDL-
DDYCNGRSAGCPRNPFH, wherein the symbols for the amino acids have their accepted biochemical meanings as follows:

| Symbol | Amino Acid Residue |
|--------|--------------------|
| K | Lysine |
| H | Histidine |
| R | Arginine |
| D | Aspartic acid |
| N | Asparagine |
| T | Threonine |
| S | Serine |
| E | Glutamic Acid |
| Q | Glutamine |
| P | Proline |
| G | Glycine |
| A | Alanine |
| C | Half-cystine |
| V | Valine |
| M | Methionine |
| I | Isoleucine |
| L | Leucine |
| Y | Tyrosine |
| F | Phenylalanine |
| W | Tryptophan |

The invention is also directed to preparations of trigramin substantially free of phospholipase A contamination, for inhibiting fibrinogen-induced aggregation of human platelets.

The invention also pertains to a method for inhibiting fibrinogen binding to human platelets and inhibiting fibrinogen-induced aggregation of human platelets. According to the method, human platelets are incubated with a preparation containing trigramin in substantially pure chemical form. Thus, trigramin may be administered to a human being to inhibit the occurrence of platelet aggregation in the bloodstream of that person.

DETAILED DESCRIPTION OF THE INVENTION

Trigramin is purified by first obtaining a crude preparation containing phospholipase A activity according to Ouyang et al., Biochim. Biophys. Acta 757:332–341 (1983). Final purification of trigramin to chemical homogeneity is accomplished by means of reverse phase high performance liquid chromatography "HPLC".

PREPARATION OF CRUDE MATERIAL

The venom of *Trimeresurus gramineus* is collected, centrifuged, lyophilized and stored in a desiccator containing anhydrous $CaCl_2$ at $-20°$ C. The venom is first separated into twelve fractions by means of DEAE-SEPHADEX A-50 column chromatography as follows. DEAE-SEPHADEX A-50 column chromatography: 1 g of the venom is applied to a column (3.2×100 cm) packed with DEAE-SEPHADEX A-50. A first stage gradient elution is carried out with 1000 ml of 0.005M ammonium acetate (pH is adjusted to 8.0 with aqueous ammonia) in the mixing vessel and 1000 ml of 0.25M ammonium acetate (pH is adjusted to 6.0 with glacial acetic acid) in the reservoir. A second stage gradient elution is carried out with 800 ml of 0.25M ammonium acetate (pH 6.0) in the mixing vessel and 1000 ml of 1M ammonium acetate (pH 5.2) in the reservoir. The flow rate is adjusted to 16–18 ml/h, and eluates of 6 ml per tube are collected. The effluent is monitored continuously at 278 nm and 5° C. with a spectrophotometer (e.g. "LKB UVICORD", LKB Company).

The venom is separated into twelve fractions according to the above DEAE-SEPHADEX A-50 column chromatography. Eight fractions are obtained in the first stage gradient elution, while the other four fractions are obtained in the second stage elution. Fraction 12 is then refractionated on a SEPHADEX G-75 column as follows: SEPHADEX G-75 Chromatography: The column comprises SEPHADEX prepared in 0.005M ammonium bicarbonate (pH 7.8). The size of the column is according to the amount of venom. Elution from the SEPHADEX G-75 column is carried out with 0.005M ammonium bicarbonate. The flow rate is adjusted to 18 ml/h. Eluates of 3 ml per tube are collected. SEPHADEX G-50 Chromatography: The third subfraction from the SEPHADEX G-75 column possessing inhibitor activity on platelet aggregation induced by thrombin (0.1 U/ml) is refractionated on Sephadex G-50 three times until a single peak is obtained. Ammonium bicarbonate (0.005M, pH 7.8) is used as the eluent. The resulting crude material is further purified as follows.

Purification of Trigramin To Chemical Homogeneity

A high performance liquid chromatography column (250×4.6 mm) containing a wide-pore C-18 silica matrix (e.g., VYDAC TPRP, The Separations Group, Hesperia, Calif.) is equilibrated at 20° C. in 0.1% trifluoroacetic acid. 150 micrograms of the above-prepared crude material in 200 microliters of 0.15M NaCl is injected into the column at a flow rate of 1.0 ml/min. The column is washed for 3 minutes. Fractions are eluted over 50 minutes with a gradient of 0–55% acetonitrile. The first component eluting after a retention time of 37 minutes comprises pure trigramin, devoid of phospholipase A activity. The homogeneity of the purified material is confirmed by SDS-polyacrylamide gel electrophoresis with a silver stain (1 microgram). Trigramin appears as a single band with apparent molecular weight of about 9 kd on 20% gels.

The amino acid sequence of the HPLC-purified trigramin is determined after pyridylethylating the material to convert cysteine residues to S-pyridylethyl-cysteine, a cysteine derivative stable during Edman degradation. Intact S-pyridylethyl-trigramin is subjected to $NH_2$-terminal sequencing which yields 35 unambiguous residues. Further sequencing is accomplished by deliberate proteolytic cleavage of the S-pyridylethyl-trigramin by chymotrypsin, trypsin and *S. aureus* V8 protease, and sequencing of individual separated cleavage fragments. The complete sequence for the 72 amino acid residues of trigramin is thus obtained.

Trigramin inhibits platelet aggregation by specifically and competitively inhibiting fibrinogen binding to fibrinogen receptors on platelets associated with the GPIIb-GPIIIa complex, which receptors are exposed by ADP. Trigramin further inhibits binding of von Willebrand factor, which, along with fibrinogen, induces platelets to aggregate or adhere to surfaces. Our experiments provide evidence that trigramin binds specifically to the GPIIb-GPIIIa complex, and that it competitively blocks fibrinogen and von Willebrand factor binding to the receptors associated with the complex.

Trigramin Inhibition of Fibrinogen Binding to Platelets

The following experiment illustrates that trigramin can inhibit fibrinogen binding to platelets. Human washed platelet suspension was prepared according to the method of Mustard et al., Brit. J. Haemat. 22:193–204 (1972) and suspended in Tyrode's albumin solution (pH 7.35) containing 3.5 mg/ml bovine serum albumin (Sigma, Fraction V). To 420 microliters of this platelet suspension (about $5 \times 10^8$ platelets/ml) was added 10 microliters of $^{125}$I-fibrinogen. An amount of trigramin was added to the suspension, followed 3 minutes later by 10 microliters ADP (final concentration 10 micromolar). Following addition of ADP, the platelet suspension was gently shaken and incubated for about another 10 minutes. Then, 400 microliters of the platelet suspension were centrifuged through silicone oil at 15,000 g in an Eppendorf centrifuge. The amount of $^{125}$I-fibrinogen bound to the platelet pellet was measured. Nonspecific binding of fibrinogen was measured in the presence of 6 mM EDTA. The $IC_{50}$ or 50% inhibition of fibrinogen binding was determined.

Figure 1:
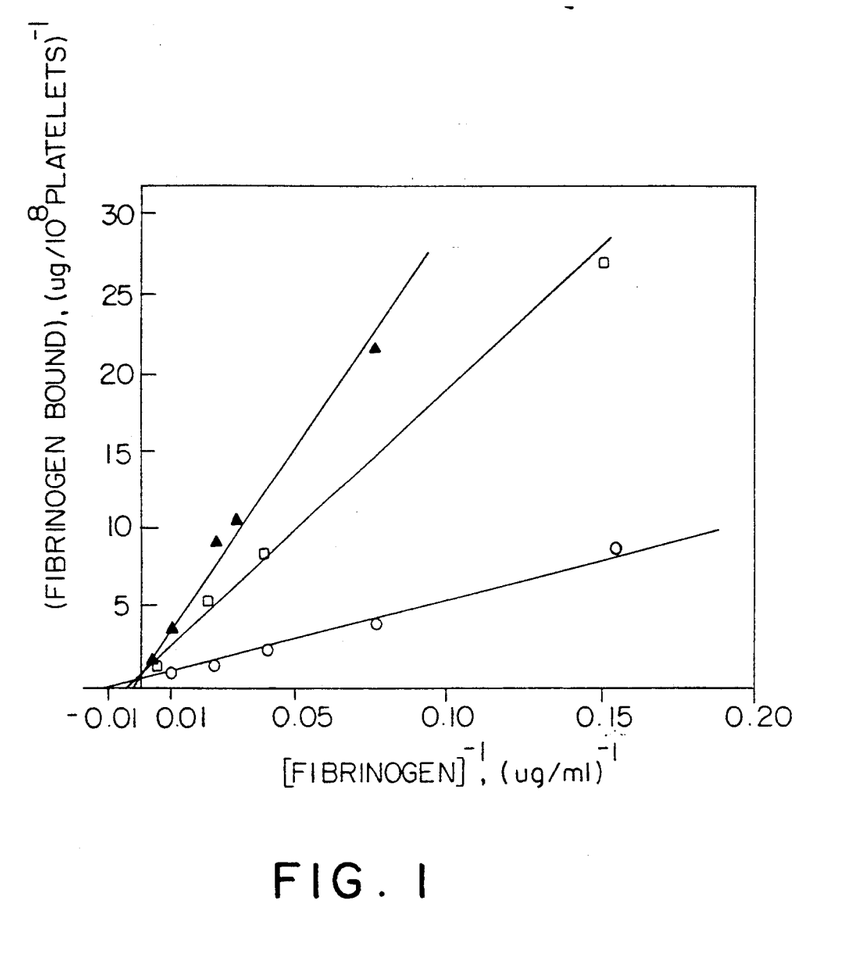
FIG. 1 is a double-reciprocal plot of $^{125}$I-fibrinogen binding to human platelets stimulated by 10 micromolar ADP in the absence (o—o) or presence of trigramin (0.5 microgram/ml, □—□; 1.0 microgram/ml, ▲—▲.

As shown in FIG. 1 trigramin inhibited $^{125}$I-fibrinogen binding to ADP (10 micromolar)-stimulated platelets in a concentration-dependent manner with an $IC_{50}$ of $2.8–5.6 \times 10^{-8}$M. The data is consistent with a competitive inhibitory mechanism of trigramin, with an inhibition constant, $K_i$, of $2 \times 10^{-8}$M.

Trigramin is also observed to inhibit $^{125}$I-fibrinogen binding to alpha-chymotrypsin-treated platelets with an $IC_{50}$ of $1.1 \times 10^{-8}$M, thus indicating its direct effect on the exposed fibrinogen receptors (data not shown). Reduced trigramin ($2 \times 10^{-6}$M) did not inhibit $^{125}$I-fibrinogen binding of ADP-stimulated platelets (data not shown).

Trigramin Inhibition of Platelet Aggregation in Isolated Platelet Suspension The following experiments demonstrate the effectiveness of trigramin in inhibiting platelet aggregation of ADP-stimulated and chymotrypsin-treated platelets. Platelet suspension was prepared as above. Platelets treated with alpha chymotrypsin (Sigma, grade IS)

were prepared as described by Kornecki et al., J. Biol. Chem. 258:9349-9356 (1983), except that the incubation time of the platelets with chymotrypsin was reduced from 45 minutes to 20 minutes.

Figure 2:
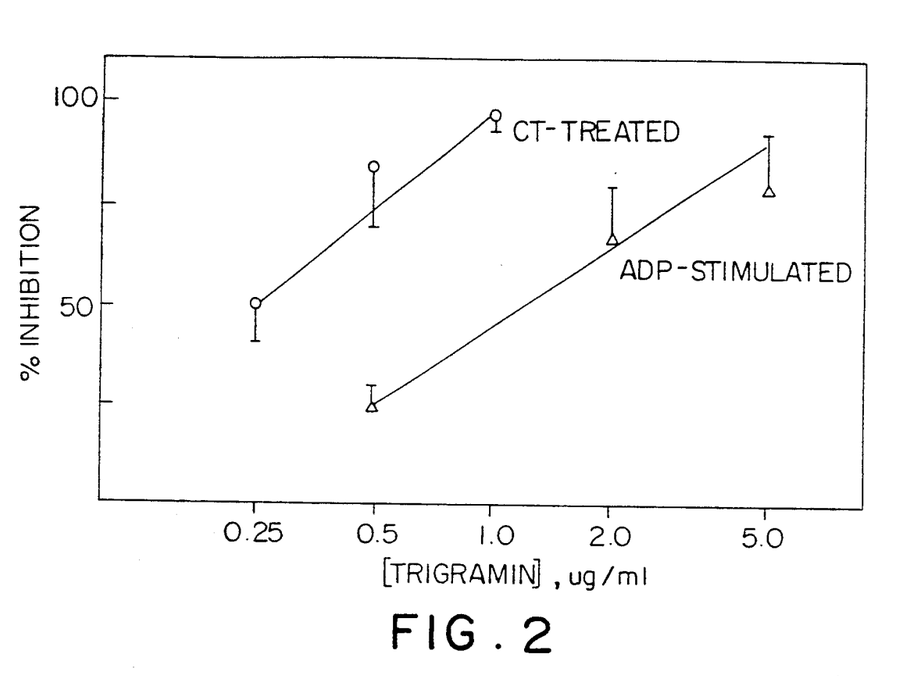
FIG. 2 is a plot of the concentration-dependent inhibitor effect of trigramin on fibrinogen-induced platelet aggregation of ADP-stimulated platelets (Δ—Δ) or chymotrypsin (CT)-treated platelets (o—o). 200 micrograms/ml fibrinogen and 10 micromolar ADP were used. Each data point represents the mean of at least five experiments.

Various doses of trigramin (0.25-5.0 microgram/ml) were added to 420 microliters of platelet suspension ($3 \times 10^8$ platelets per ml). One minute later, 10 microliters ADP (10 micromolar) and 10 microliters fibrinogen (200 micrograms) were added to initiate platelet aggregation. The same procedure using fibrinogen alone (without ADP) was carried out to induce aggregation of the chymotrypsin-treated platelets. The extent of platelet aggregation in each system was measured at 37° C. by the turbidimetric method of Born et al., J. Physiol. (Lond.) 168:178-195 (1963). The $IC_{50}$ value for trigramin inhibition of aggregation of ADP-stimulated platelets was $1.3 \times 10^{-7}$M. The $IC_{50}$ value for trigramin inhibition of chymotrypsin-treated platelets was $2.8 \times 10^{-8}$M. The data is shown in FIG. 2.

It is known that chymotrypsin-treated platelets interact with fibrinogen directly since they have fibrinogen receptors exposed on the surface. Without wishing to be bound by any theory, the inhibitor effect of trigramin on fibrinogen-induced aggregation of chymotrypsin-treated platelets indicates that trigramin interacts directly with fibrinogen receptors on the platelet membranes.

Trigramin also inhibited platelet aggregation induced by the stable prostaglandin endoperoxide analogue 9,11-dideoxy-9,11-methanoepoxy-$PGF_2$-alpha (2.5 micromolar) and by thrombin (0.5 units/ml) in a concentration-dependent manner.

In platelet-rich plasma, trigramin inhibited platelet aggregation induced by ADP (10 micromolar), epinephrine (50 micromolar), 9,11-dideoxy-9,11-methanoepoxy-$PGF_2$-alpha (2.5 micromolar) and sodium arachidonate (200 micromolar) with an $IC_{50}$ of $2-4 \times 10-7$M.

There are several similarities between the binding of $^{125}$I-trigramin and the binding of $^{125}$I-fibrinogen to human platelets. The binding of both ligands is inhibited by EDTA; by monoclonal antibodies interacting with the GP-IIb-GPIIIa complex (Coller, J. Clin. Invest. 76:101-108 (1985) and Bennett et al., Proc. Natl. Acad. Sci. U.S.A. 80:2417-2421 (1983)); by synthetic peptides representing putative platelet binding sites on the fibrinogen molecule Arg-Gly-Asp-Ser (Gartner et al., J. Biol. Chem. 260:11891-11894 (1985) and Plow et al., Proc. Natl. Acad. Sci. U.S.A. 82:8057-8061 (1985)); and by tyrosyl pentadecapeptide of the C-terminal portion of the gamma chain, Gly-Gln-Gln-His-His-Leu-Gly-Gly-Ala-Lys-Gln-Ala-Gly-Asp-Val (Kloczewiak et al., Biochemistry 23:1767-1774 (1984). Neither trigramin nor fibrinogen was observed to bind sufficiently to platelets of patients with Glanzmann's thrombasthenia. These individuals are deficient in the GPIIb-GPIIIa complex. Fibrinogen does not bind to resting platelets, and the stimulation of platelets by ADP or treatment with proteolytic enzymes is a requirement for the exposure of fibrinogen binding sites. On the other hand, the number of trigramin binding sites on resting platelets, on ADP-stimulated platelets, and on chymotrypsin-treated platelets is similar, and amounts to 50% of the total number of fibrinogen binding sites exposed by ADP.

The binding affinity of $^{125}$I-trigramin to ADP-stimulated platelets, as judged on the basis of dissociation constants, is approximately 15-fold greater than the binding affinity of $^{125}$I-fibrinogen to ADP-stimulated platelets. Thus, it was observed that both monoclonal antibodies and synthetic peptides inhibit fibrinogen binding to platelets more effectively than trigramin binding to ADP-stimulated platelets. The binding affinity of trigramin to ADP-stimulated platelets resembles that of monoclonal antibodies. It is several orders of magnitude higher than binding affinity of synthetic peptides to platelets.

Figure 5:
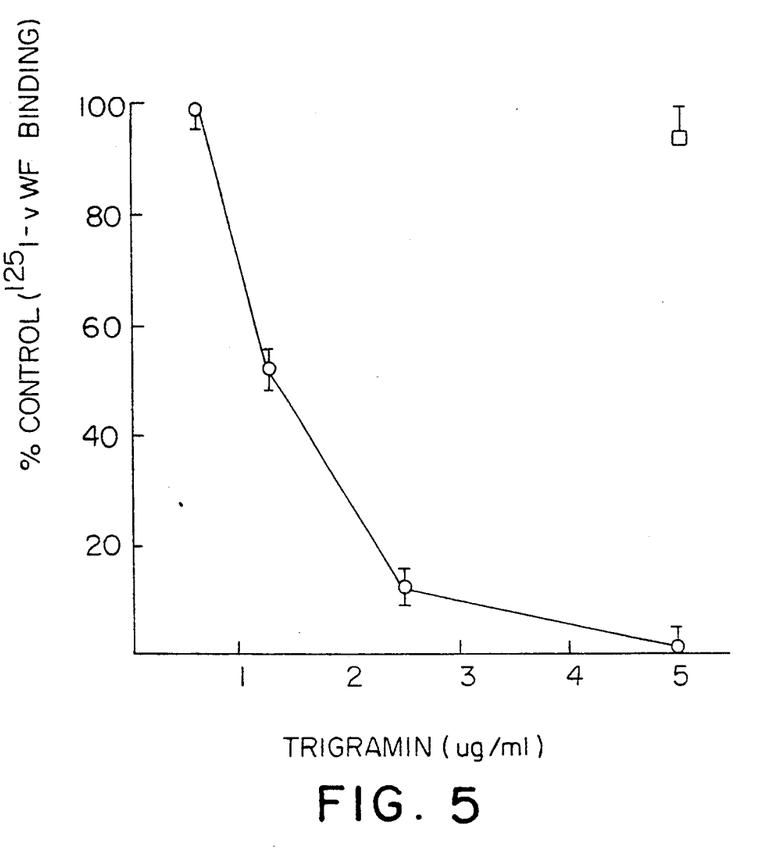
FIG. 5 is a plot of trigramin inhibition of the binding of $^{125}$I-von Willebrand Factor to thrombin (0.5 U/ml)-activated platelets (o—o) and ristocetin (0.75 mg/ml)-induced platelets (□—□).

We have also demonstrated that trigramin at a concentration of $10^{-8}$M specifically blocks the binding of highly purified von Willebrand Factor to thrombin-stimulated human platelets. FIG. 5 shows the effect of trigramin on $^{125}$I-von Willebrand Factor binding to thrombin (0.5 u/ml)-stimulated platelets. The final concentration of von Willebrand Factor was 5 micrograms/ml. The total specific von Willebrand Factor binding was $380 +/- 55$ ng/$10^8$ platelets in the control sample. By contrast, trigramin does not block binding of von Willebrand Factor to ristocetin (0.75 mg/ml)-stimulated platelets (control, $754 +/- 140$ ng/$10^8$ platelets). It is well known that von Willebrand Factor binds to GPIIb-GPIIIa complex on thrombin-stimulated platelets, and to GPIb on ristocetin-stimulated platelets. We conclude that trigramin does not block binding of von Willebrand factor to GPIb.

Without wishing to be bound by any theory, trigramin may bind to the same epitope as fibrinogen in the GPIIb-GPIIIa complex, or it may bind in close proximity to the fibrinogen receptor epitope.

We have also observed an interaction between trigramin and melanoma cells that contain GPIIIa and vitronectin receptor. Trigramin blocks the adhesion of the cells to fibronectin-covered substrata and inhibits cell spreading. In the system tested, the biological activity of 0.2 nmoles of trigramin corresponded to 100 nmoles of the peptide glycine-arginine-glycine-aspartic acid-serine ("GRGDS"). This observation is interesting in view of the successful efforts of Humphries et al., Science 233: 467-470 to inhibit metastases of a melanoma cell line in mice by GRGDS.

Conventional methods of inhibiting platelet aggregation rely on inhibition of platelet stimulation. Trigramin, on the other hand, acts as a direct competitive inhibitor of fibrinogen binding, which causes platelet aggregation. While monoclonal antibodies to the GPIIb-GPIIIa complex are potent platelet aggregation inhibitors, monoclonal antibodies are exceptionally large molecules. They typically have molecular weights of 180 kd or more. Such molecules are known to be immunogenic in humans, particularly monoclonal antibodies of murine origin.

Trigramin, on the other hand, is a relatively small polypeptide of molecular weight of 8 kd. Thus, trigramin is expected to be far less immunogenic than monoclonal antibodies. Moreover, the action of trigramin in competitively inhibiting binding of fibrinogen to the GPIIb-GPIIIa complex is highly specific. Trigramin has the epitope specificity and high binding affinity of a monoclonal antibody without the attendant immunogenicity.

Trigramin may be administered in any situation where inhibition of formation of hemostatic platelet plugs is desired.

Trigramin appears to be eliminated from the circulation rapidly. Trigramin is particularly useful in inhibiting platelet aggregation in situations where a strong blood anticoagulant of short duration of effectiveness is needed.

Thus, trigramin may find utility in surgery on peripheral arteries (arterial grafts) and in cardiovascular surgery where manipulation of arteries and organs, and the interaction of platelets with artificial surfaces, leads to platelet aggregation and consumption. The aggregated platelets may form thromboemboli. Trigramin may be administered to these surgical patients to prevent platelet consumption.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al, Amer. J. Physiol. 252:H615–621, 1987). Platelets released from artificial surfaces show impaired hemostatic function. Trigramin may be administered to prevent adhesion.

It is of interest that trigramin does not interfere with the interaction between glycoprotein Ib on the platelet membranes and von Willebrand Factor, which is critical for efficient hemostasis in wounds. Because of this, and because the hemostatic effect of trigramin is short lived, trigramin will not interfere with the resumption of normal hemostasis in a surgical patient. A rapid return to normal bleeding time occurs with cessation of trigramin adminstration.

Other applications of trigramin may include prevention of platelet thromboembolism after cessation of thrombolytic therapy and prevention of platelet thromboembolism after angioplasty of coronary and other arteries. In many clinical centers patients subjected to these procedures are already receiving antiplatelet drugs which are weaker inhibitors of platelet aggregation as compared to trigramin.

Trigramin may be useful for preventing the spread of certain tumor cells (e.g. melanoma) and metastases. This is because trigramin has been observed to inhibit adhesion and spreading of a melanoma cells.

Trigramin may be administered by any convenient means which will result in its delivery into the blood stream in substantial amount. Intravenous administrations is presently contemplated as the preferred administration route. Trigramin is soluble in water, and may therefore be effectively administered in solution.

Trigramin is relatively stable to proteolysis, thus, oral administration is feasible. Oral administration may take the form of tablets, capsules, etc. of trigramin formed with suitable binder materials.

The in vivo effect of trigramin is demonstrated by the following hamster study.

HAMSTER STUDY

Female golden Syrian hamsters (90–150 g) were maintained on food and water ad libitum, but fasted overnight prior to their use in the present experiment. After the administration of anesthesia (65 mg/kg sodium pentobarbital, i.p.), the animals were shaved in preparation for surgery. The trachea was intubated with PE-100 polyethylene tubing to facilitate spontaneous breathing. Cannulation of the right femoral vein was performed to provide an intravenous route for supplemental anesthesia as well as for the administration of various control and experiment agents. A catheter was introduced into the right carotid artery for the continuous monitoring of arterial blood pressure, and a rectal temperature probe was inserted. The animal's body temperature was maintained at 37° C. with a heating pad and lamp.

The shaved abdomen was opened by a mid-line incision and a portion of the small intestine was exteriorized and draped over a lucite pedestal. Exposed tissue was kept warm and moist by continuous superfusion with warmed (37° C.) Mammalian Ringer's Solution. Experimental solutions were infused into the right femoral vein at a rate of 0.199 ml/min with a Harvard pump for a 10 minute period. An arterial vessel (external diameter, 100–200 micrometers) located at the junction of the small intestinal wall and the mesentery was severed 4 minutes after the start of the infusion. Blood was flushed away by the superfusion system and the waste was removed with a vacuum from a well surrounding the viewing pedestal. Bleeding was observed through Zeiss dissecting microscope (20×) and bleeding time was recorded from the time of the cut until the cessation of bleeding by the formation of a hemostatic plug. Each animal was used as its own control with bleeding time determined both during the infusion of saline and the selected experimental agent. Six animals were evaluated with a second saline infusion substituted for trigramin to insure that repeated measurements did not influence the subsequent bleeding time responses. No differences were found between the mean bleeding times of these two saline infusions. Four additional animals were infused with trigramin while arterial blood pressure was continuously monitored to determine if it had any direct effect on systemic blood pressure. One hamster was administered the $PGI_2$ analogue (2 ng/kg/min) Iloplrost (Benlex Laboratories, Cedar Knolls, N.J.) to serve as a positive control. In this animal, bleeding did not cease until approximately 9 minutes after the completion of the infusion.

Figure 3:
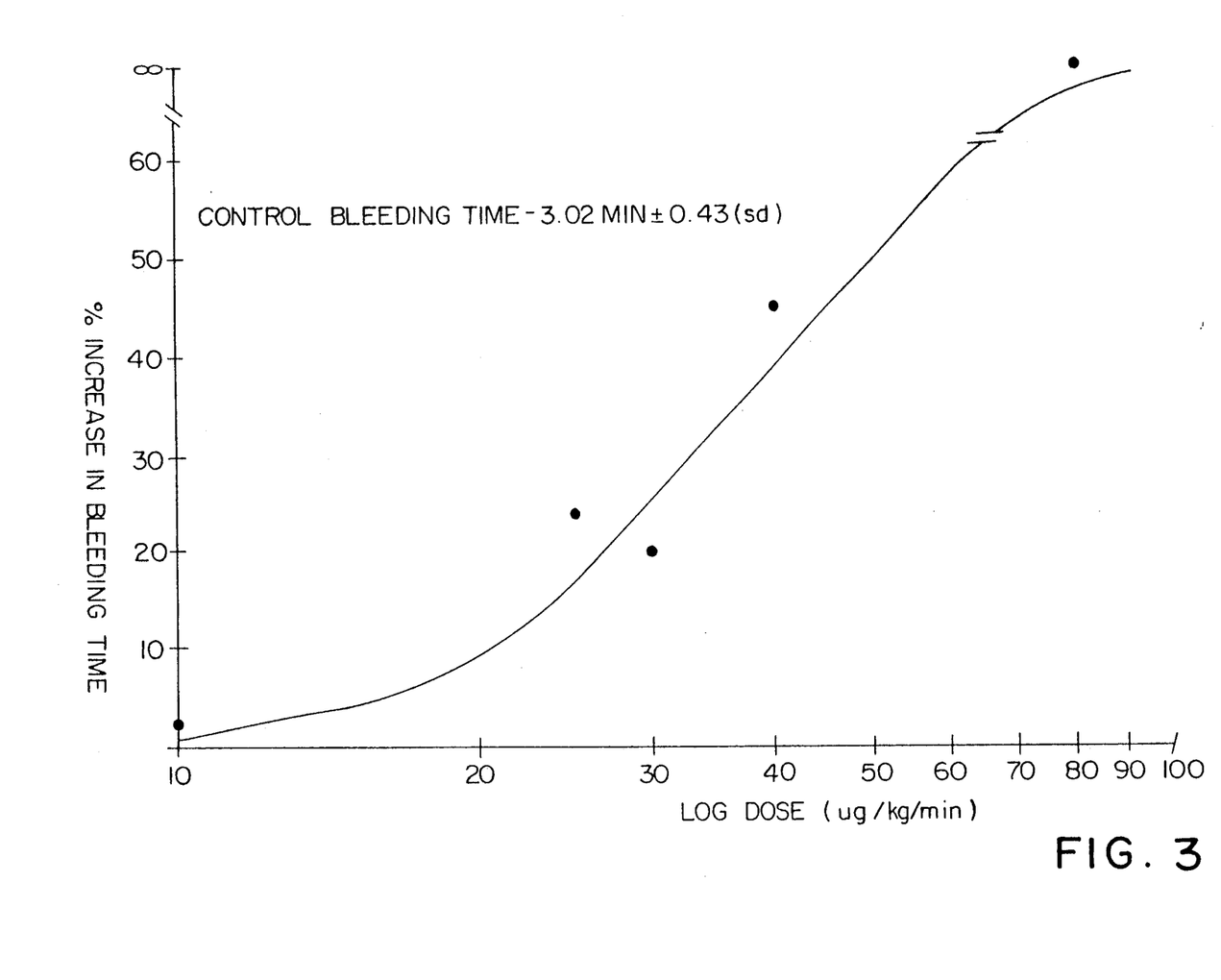
FIG. 3 is a plot of the in vivo effect of continuous infusion of trigramin on bleeding time of hamsters from a mesentery lesion.
Figure 4:
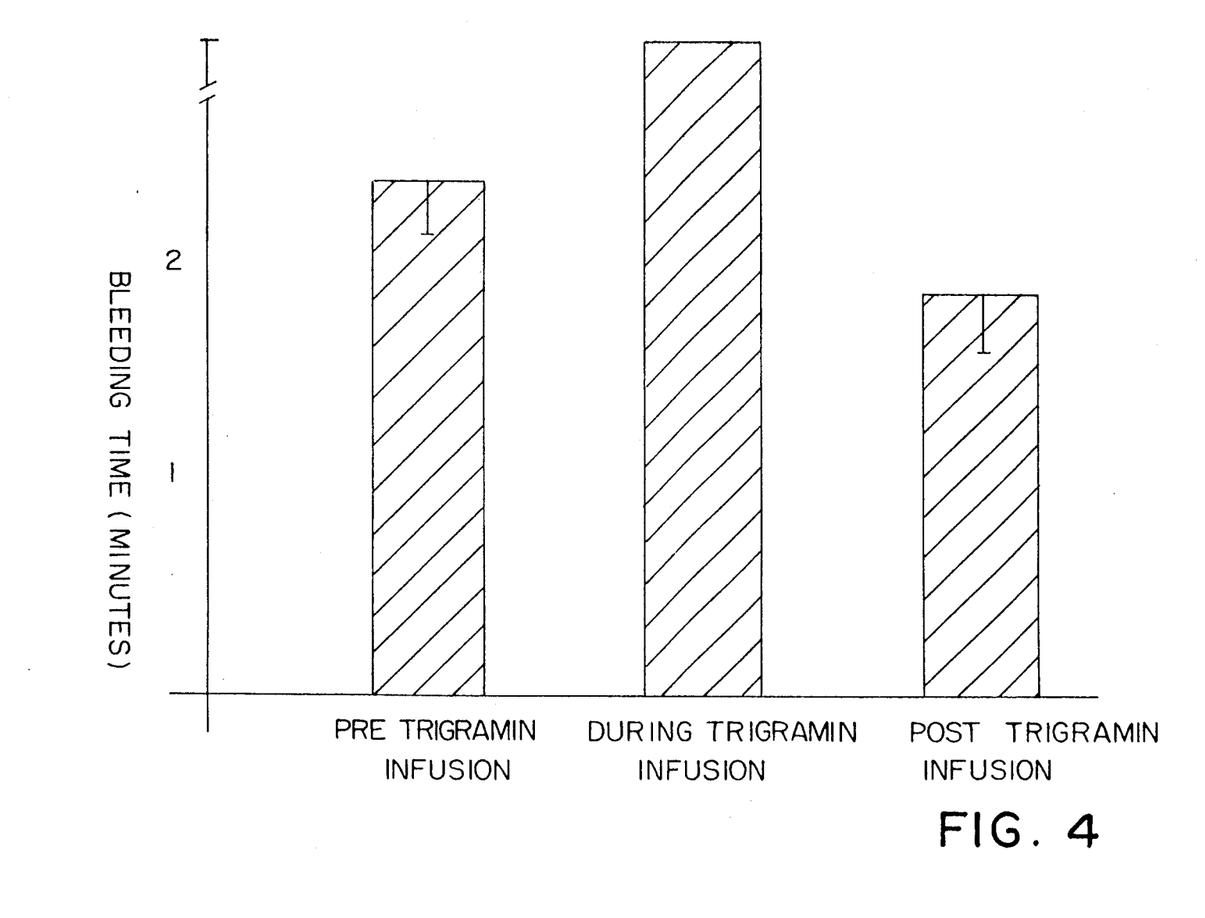
FIG. 4 is a bar graph of the bleeding time from the hamster mesentery before, during and after infusion of trigramin (80 micrograms/kg/min).

Trigramin infused continuously markedly increased the bleeding time of the hamster mesentery in dose-dependent fashion, based upon a control bleeding time of 3.02 minutes+/−0.43. See FIG. 3. Cessation of trigramin infusion caused a rapid return of bleeding time to normal values. See FIG. 4.

We have succeeded in isolating trigramin from the venom of *Trimeresurus gramineus*. It is understood that proteins which may be isolated from other Trimeresurus species according to the herein purification method, which proteins have the same or substantially the same amino acid sequence as the molecule described herein, are included in the scope of the present invention.

Purification of trigramin to chemical homogeneity according to the present invention has permitted amino acid sequencing of the molecule. While the molecule has in the first instance been purified from a natural source, *T. gramineus* venom, it is contemplated that trigramin may also be prepared through genetic engineering techniques known to those skilled in the art. Thus, based upon the amino acid sequence of trigramin being disclosed herein, one may advantageously prepare a synthetic gene corresponding to said amino acid sequence and introduce that gene into an appropriate host by appropriate cloning vectors. Alternatively, it is contemplated that pure trigramin may be prepared by obtaining the natural gene from venom-producing cells of *T. gramineus*, followed by recombination and cloning. It is therefore understood that the scope of the invention is not merely limited to trigramin isolated by following the chromatographic procedures disclosed herein, but also includes trigramin as it may be prepared by genetic engineering techniques.

The present invention may be embodied in other specific forms without departing from the spirit or essential attributes thereof and, accordingly, reference should be made to the appended claims, rather than to the foregoing specification, as indicating the scope of the invention.

We claim:

1. The polypeptide in substantially pure chemical form having the following amino acid sequence:
EAGEDCDCGSPANPCCDAATCKLIPGAQCGEGLCCDQCSFIEEGTVCRIARGDDLDDYCNGRSAGCPRNPFH.

2. A preparation for inhibiting fibrinogen-induced aggregation of human platelets comprising the polypeptide EAGEDCDCGSPANPCCDAATCKLIPGAQCGEGLCCDQCSFIEEGTVCRIARGDDLDDYCNGRSAGCPRNPFH, said preparation being free of phospholipase A contamination.

3. A method of inhibiting fibrinogen binding to human platelets or fibrinogen-induced aggregation of human platelets comprising incubating human platelets with the polypeptide according to claim 1.

4. A method of inhibiting fibrinogen binding to human platelets or fibrinogen-induced aggregation of human platelets comprising incubating human platelets with the preparation of claim 2.

5. A method of inhibiting aggregation of platelets in a human being comprising administering to that person a polypeptide according to claim 1 to inhibit the occurrence of platelet aggregation in the bloodstream of said person.

* * * * *